United States Patent [19]

Williams et al.

[11] Patent Number: 5,023,225

[45] Date of Patent: Jun. 11, 1991

[54] DEHYDROGENATION CATALYST AND PROCESS FOR ITS PREPARATION

[75] Inventors: David L. Williams; Karl J. Russ; Edward K. Dienes; George A. Laufer, all of Louisville, Ky.

[73] Assignee: United Catalysts Inc., Louisville, Ky.

[21] Appl. No.: 383,177

[22] Filed: Jul. 21, 1989

[51] Int. Cl.$^5$ .................. B01J 23/10; B01J 23/78; B01J 23/86

[52] U.S. Cl. .................. 502/304; 502/302; 502/303; 502/306; 502/316; 585/445

[58] Field of Search .............. 502/316, 302, 303, 304, 502/306; 585/445, 631

[56] References Cited

U.S. PATENT DOCUMENTS

| | | | |
|---|---|---|---|
| 2,426,829 | 9/1947 | Kearby | 502/330 X |
| 3,360,579 | 12/1967 | Hills et al. | 502/174 x |
| 3,703,593 | 11/1972 | Turley et al. | 502/316 |
| 4,467,046 | 8/1984 | Smith et al. | 502/304 X |
| 4,628,137 | 12/1986 | Chu | 585/445 |

*Primary Examiner*—W. J. Shine
*Attorney, Agent, or Firm*—Herbert P. Price

[57] ABSTRACT

Improved iron oxide catalysts for the dehydrogenation of ethylbenzene to styrene are made by forming a blend of chromium oxide and yellow iron hydrate and heating the blend to convert the yellow iron hydrate to red iron oxide prior to forming the catalyst.

15 Claims, 3 Drawing Sheets

DEHYDROGENATION CATALYST AND PROCESS FOR ITS PREPARATION

BACKGROUND OF THE INVENTION

The field of art to which this invention pertains is dehydrogenation catalysts.

In the catalytic dehydrogenation of alkyl aromatic hydrocarbons to alkenyl aromatic hydrocarbons, e.g., ethyl benzene to styrene, considerable efforts have been expended to develop catalysts which exhibit not only good conversion properties but also high selectivity as well as increased stability.

Typical catalysts used in dehydrogenation of saturated hydrocarbons to unsaturated hydrocarbons, as disclosed in U.S. Pat. No. 2,866,790, are iron oxide catalysts containing a small amount of chromium oxide as a stabilizer and a small amount of potassium compound as promoter. Improved catalysts according to this patent are made from iron oxide (39–47 weight percent), chromium oxide (1–10 weight percent) and potassium carbonate (51–59 weight percent).

Dehydrogenation catalysts having good physical strength are described in U.S. Pat. No. 2,866,791. These catalysts are made from 10 to 60 weight percent potassium fluoride, 0.2 to 20 weight percent chromium oxide and the balance iron oxide.

According to U.S. Pat. No. 3,360,579, a dehydrogenation catalyst, which contains 80–90 weight percent iron oxide, 9–18 weight percent potassium carbonate and 1.5 to 5 weight percent chromium oxide, is prepared by combining yellow iron oxide, chromium oxide, potassium carbonate and water to form a paste, extruding the paste to form pellets, drying the pellets and calcining them at 800°–1000° C. A catalyst made in a similar manner is described in U.S. Pat. No. 3,364,277.

Catalysts having good activity and good selectivity are described in U.S. Pat. No. 3,904,552. These catalysts are made with iron oxide and alkali metal oxides plus molybdenum oxide and cerium oxide.

U.S. Pat. No. 4,404,123 discloses dehydrogenation catalysts which contain iron oxide, potassium oxide, gallium trioxide and 0–5 weight percent chromium oxide.

Other patents which disclose dehydrogenation catalysts based on iron oxide are U.S. Pat. Nos. 4,467,046, 4,749,674, 4,758,543 and 4,804,799.

Dehydrogenation reactions are normally conducted at the highest practical throughput rates to obtain optimum yield. Yield is dependent on conversion and selectivity of the catalyst.

Selectivity of the catalyst is defined as the proportion of the desired product, e.g., styrene, produced to the total amount of feedstock, e.g., ethylbenzene, converted. Activity or conversion is that portion of the feedstock which is converted to the desired product and to by-products.

Improvements in either selectivity or activity but particularly the selectivity of a dehydrogenation catalyst can result in substantially improved operating efficiency.

Low selectivity results in high by-product formation. In the dehydrogenation of ethylbenzene to styrene, the predominant by-products are benzene and toluene. The benzene produced can be recycled for later processing. Toluene cannot be easily recycled and is considered an undesirable by-product. The ratio of benzene to toluene (B/T) in the final product is another criteria to be used in determining the effectiveness of the catalyst.

The activity of dehydrogenation catalysts diminishes with time. Ultimately, the activity of the catalyst is reduced to the point where the catalyst must be regenerated or be replaced. Regeneration and replacement of the catalysts are expensive due to lost production and cost of the catalyst. Any increase in stability of the catalyst, i.e., long term use without diminished activity or selectivity, enhances the economics of the process using the catalyst.

The incorporation of chromium oxide in iron oxide dehydrogenation catalysts, such as those described in U.S. Pat. No. 2,866,790, has been known to improve the stability of the catalysts. However, opposite results are obtained when chromium oxide is added to improved dehydrogenation catalysts, such as those disclosed in U.S. Pat. No. 3,904,552. These catalysts which are described as molybdenum and cerium promoted iron oxide catalysts exhibit improved selectivity and activity in dehydrogenation reactions over iron oxide catalysts which do not contain the promoters. The addition of chromium oxide to such catalysts, rather than improving the stability, actually reduces the time during which the catalysts are effective.

SUMMARY OF THE INVENTION

This invention is directed to dehydrogenation processes. In one aspect, this invention pertains to a dehydrogenation catalyst having improved activity and selectivity over time in operation. In another aspect, this invention relates to a process for preparing the dehydrogenation catalyst. In yet another aspect, this invention pertains to a dehydrogenation process using the improved catalyst.

The catalyst of this invention is predominantly an iron oxide catalyst containing chromium oxide modification wherein the chromium oxide modification is obtained prior to the formation of the catalyst by either precipitating a chromium salt or chromium oxide with the iron in the formation of yellow iron hydrate or blending chromium oxide or a chromium salt with yellow iron hydrate followed by converting the yellow iron hydrate with heat to red iron oxide. Sufficient chromium compound is added in order to obtain about 100 to about 5,000 ppm chromium in the red iron oxide wherein the ppm is based on the weight of chromium and weight of red iron oxide.

In addition to iron oxide and chromium oxide, the catalyst of this invention contains alkali metal oxides, alkaline earth metal oxides, oxides of the cerium subgroup having atomic numbers of 57 to 62, and molybdenum or tungsten oxide.

The catalyst of this invention is particularly useful for dehydrogenating alkyl aromatic hydrocarbons to alkenyl aromatic hydrocarbons.

DESCRIPTION OF THE DRAWINGS

Referring to the drawings.

DESCRIPTION OF THE INVENTION

Figure 1:
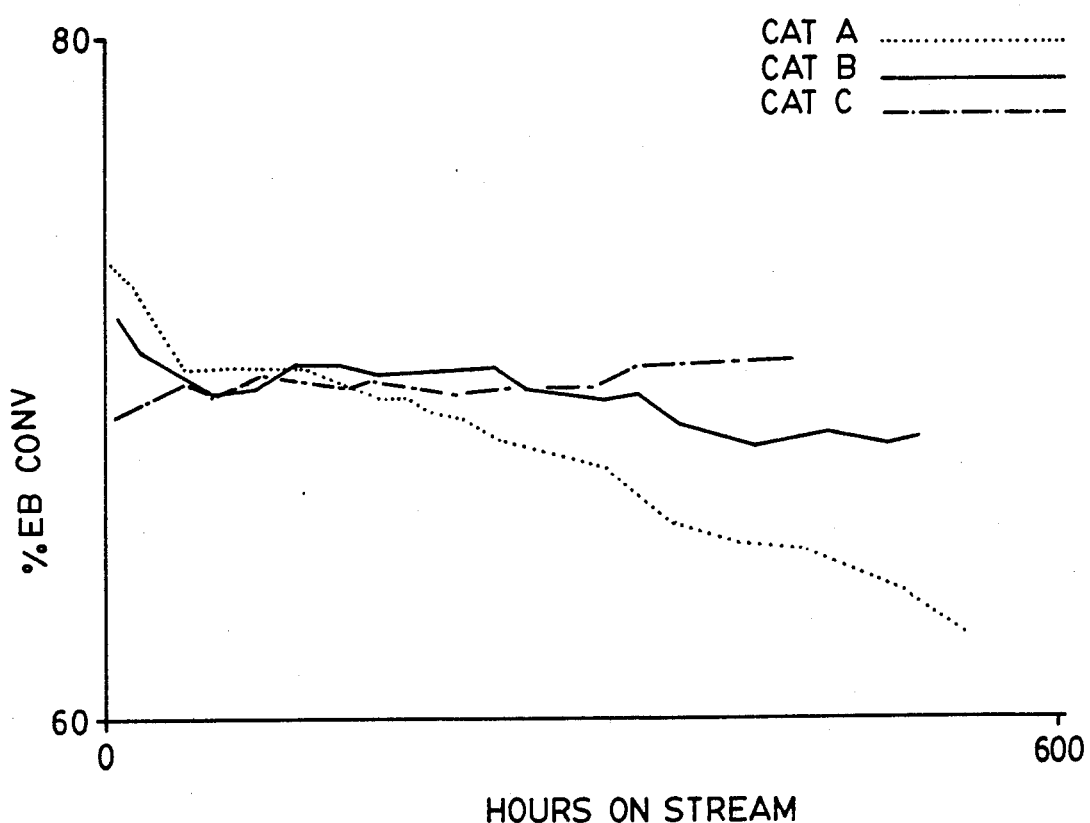
FIG. 1 and FIG. 2 are plots of the weight percent ethyl benzene conversion versus hours on stream using catalyst containing chromium oxide which had been added to yellow iron hydrate before conversion to red iron oxide and catalysts which contained no chromium oxide.

Yellow iron hydrate, which is blended with chromium oxide prior to conversion to red iron oxide, is the hydrated form of ferric oxide and is essentially ferric oxide monohydrate. Yellow iron hydrate can be made by the controlled oxidation and precipitation of ferrous sulfate solutions, such as disclosed in U.S. Pat. No. 2,111,726.

As described in U.S. Pat. No. 2,111,726, which is hereby incorporated by reference, an aqueous solution of a water soluble iron salt, e.g., ferrous sulfate, is treated with an oxidizing agent, e.g., air, and a base to precipitate yellow iron hydrate. The yellow iron hydrate is then heated at about 500° C. to about 1000° C. for a time sufficient to drive off the water of hydration and to convert the yellow iron hydrate to red iron oxide. For use in the catalysts of this invention, the yellow iron hydrate is modified with chromium either by coprecipitation of a chromium salt with the iron or by blending a chromium salt or chromium oxide with the yellow iron hydrate after it is formed. In the coprecipitating process, a water soluble chromium salt, e.g., chromic potassium sulfate, is dissolved in the ferrous sulfate solution and coprecipitates with the iron.

In the blending process, chromium oxide or a salt of chromium is thoroughly blended with the yellow iron hydrate after it is precipitated. In both instances, the yellow iron hydrate and the chromium compound are heated at about 500° C. to about 1000° C. to convert the yellow iron hydrate to red iron oxide. The chromium salts are simultaneously converted to chromium oxide.

In addition to ferrous sulfate, other water soluble ferrous salts, such as ferrous chloride, ferrous nitrate, ferrous acetate, ferrous bromide, ferrous iodide, and the like can be used.

Soluble chromium salts other than chromic potassium sulfate can be used, examples of which are chromic sulfate, chromic chloride, sodium chromate, potassium chromate, sodium dichromate, potasium dichromate and the like. Any of these salts plus chromium oxide can be used in the blending process with the yellow iron hydrate.

The amount of chromium oxide or salt coprecipitated or blended with the yellow iron hydrate is that amount which will result in the chromium oxide modified red iron oxide containing about 100 to about 5000 ppm chromium, wherein the ppm are based on the weight of chromium in the chromium oxide and the weight of the red iron oxide.

While not wishing to be limited to any theory as to what makes the catalysts of this invention superior to those of the prior art, it is believed that the chromium oxide becomes embedded in and, possibly, becomes a part of the crystal structure of the red iron oxide and that this structure contributes to the stability and longer life of the resulting catalysts.

The catalysts of this invention are made by blending the chromium oxide modified iron oxide with alkali metal hydroxides, carbonates, or bicarbonates, alkaline earth metal oxides or hydroxides, oxides and salts of the cerium subgroup having atomic numbers of 57 to 62, and molybdenum or tungsten oxides and salts. The components are thoroughly blended with a small amount of water, pellets are formed by extrusion, and the pellets are calcined at about 500° C. to about 1000° C. for a time sufficient to drive off water, and water of hydration, or to convert or decompose the salts to oxides.

The cerium subgroup, molybdenum and tungsten salts are those which dissociate to the oxide during calcination, such salts being the hydrates, carbonates, nitrates, sulfates and the like.

The catalysts of this invention contain about 60 to about 90 weight percent red iron oxide which contains about 100 to about 5000 ppm chromium, about 5 to about 15 weight percent alkali metal oxide, about 2 to about 10 weight percent alkaline earth metal oxide, about 2 to about 10 weight percent oxides of the cerium subgroup, and about 1 to about 5 weight percent molybdenum oxide or tungsten oxide, said weight percent being based on the weight of the catalyst.

Preferred oxides in each group are:

(a) alkali metal oxides, i.e., sodium or potassium oxide with potassium oxide being most preferred;

(b) alkaline earth metal oxides, i.e., magnesium, calcium, or strontium oxide with both magnesium and calcium oxide being preferred;

(c) oxides of cerium subgroup, i.e., cerium, praseodymium, neodymium, or samarium oxide with cerium oxide being preferred;

(d) oxides of molybdenum or tungsten with molybdenum oxide being preferred.

A particularly preferred catalyst contains about 70 to about 86 percent red iron oxide which contains about 100 to about 1200 ppm chromium, about 7 to about 12 weight percent potassium oxide, about 3 to about 7 weight percent cerium oxide, about 1 to about 4 weight molybdenum oxide, about 1.5 to about 3.5 weight percent calcium oxide and about 1.5 to about 3.5 weight percent magnesium oxide.

The catalysts of this invention are especially effective in promoting the dehydrogenation of ethylbenzene to produce styrene. Such dehydrogenation reactions are generally carried out at reaction temperatures from about 500° C. to about 700° C., preferably about 540° C. to about 650° C. The use of subatmospheric, atmospheric, or superatmospheric pressures are suitable. However, based on equilibrium and selectivity considerations, it is preferred to operate at as low a pressure as is feasible. Therefore, atmospheric or subatmospheric pressure is preferred. The dehydrogenation process is conducted as a continuous operation utilizing a fixed bed which may consist of a single stage or a series of stages of the same catalyst in one or several reactors.

In the dehydrogenation process using the catalyst of this invention, steam is added to the hydrocarbon feed stock to aid in the removal of carbonaceous residues from the catalyst and to furnish heat for the reaction. Steam to hydrocarbon weight ratios from about 0.6 to about 3 or higher can be used. However, in order to conserve energy in the operation of the process, steam to hydrocarbon weight ratios (S/O) of 2 or lower are preferred.

The contact time of the reactant-containing gas with the catalyst is expressed in terms of liquid-hourly-space velocity (LHSV) which is defined as the volume of liquid hydrocarbon reactant per volume of catalyst per hour. The LHSV of the organic reactants can vary between about 0.3 hr$^{-1}$ and about 5hr$^{-1}$ and are adjusted within this range to effect the degree of conversion desired for the particular feed in question.

When used in the continuous process of dehydrogenating alkyl aromatic hydrocarbons to alkenyl aromatic hydrocarbons, the catalysts of this invention initially exhibit activity and selectivity comparable to catalysts which do not contain chromium modification. However, over time on stream, the catalysts of this invention retain activity and selectivity much longer than other catalysts. Advantages resulting from increases in selectivity and/or activity of only a few tenths of a percent are extremely significant in a commercial process which may produce millions of pounds of product per day.

The following examples describe the invention in more detail. Parts and percentages are by weight unless otherwise designated.

EXAMPLE 1

A dehydrogenation catalyst was prepared having the following chemical composition:

| | |
|---|---|
| $Fe_2O_3$ | 78.6 percent |
| $K_2O$ | 9.5 percent |
| $CeO_2$ | 5.0 percent |
| $MoO_3$ | 2.5 percent |
| CaO | 2.2 percent |
| MgO | 2.2 percent |

This catalyst was designated as Catalyst A.

Additional catalysts were made having the same composition as shown for Catalyst A except that the ferric oxide had been modified with chromium oxide prior to conversion of yellow iron hydrate to red iron oxide in the amounts, expressed as chromium, of 1000 ppm (Catalyst B) and 5000 ppm (Catalyst C), said ppm being based on the weight of chromium and ferric oxide.

Dehydrogenation reactions were conducted using ethyl benzene of 100 percent nominal purity in a tubular reactor with 100 cc. of catalyst at 1.0 LHSV, and 1.0 atmosphere. Test data from these reactions are shown in Table 1.

FIG. 1 is a plot of Percent Ethylbenzene Conversion vs. Time on Stream of Catalysts A, B and C which shows the improved stability of the catalyst of this invention.

TABLE I

Ethylbenzene Dehydrogenation

| Hours | S/O | Temp °F. | Conversion % | Yield % | Selectivity % | B/T |
|---|---|---|---|---|---|---|
| \multicolumn{7}{c}{Catalyst A} | | | | | | |
| 43.5 | 2.0 | 1150 | 75.1 | 70.5 | 93.9 | 0.31 |
| 90.5 | 2.0 | 1100 | 60.0 | 57.8 | 96.3 | 0.22 |
| 138.5 | 2.0 | 1050 | 40.9 | 39.8 | 97.4 | 0.25 |
| 212.5 | 1.5 | 1150 | 70.5 | 65.8 | 93.4 | 0.40 |
| 260.5 | 1.5 | 1150 | 70.5 | 66.1 | 93.8 | 0.41 |
| 379.5 | 1.5 | 1150 | 68.8 | 64.9 | 94.5 | 0.41 |
| 478.0 | 1.5 | 1150 | 67.3 | 63.8 | 94.7 | 0.42 |
| 595.0 | 1.5 | 1150 | 65.0 | 61.7 | 94.8 | 0.46 |
| 717.0 | 1.5 | 1150 | 62.7 | 59.3 | 94.6 | 0.52 |
| 740.5 | 2.0 | 1150 | 69.4 | 66.1 | 95.3 | 0.33 |
| 763.5 | 2.0 | 1150 | 70.1 | 66.8 | 95.2 | 0.33 |
| 798.5 | 2.0 | 1100 | 53.2 | 51.6 | 97.0 | 0.25 |
| \multicolumn{7}{c}{Catalyst B} | | | | | | |
| 43.5 | 2.0 | 1150 | 75.0 | 69.4 | 92.5 | 0.39 |
| 92.5 | 2.0 | 1150 | 74.8 | 69.9 | 93.5 | 0.35 |
| 145.5 | 1.5 | 1150 | 72.2 | 66.1 | 91.5 | 0.47 |
| 211.0 | 1.5 | 1150 | 69.6 | 65.0 | 93.4 | 0.45 |
| 260.0 | 1.5 | 1150 | 70.4 | 65.8 | 93.5 | 0.42 |
| 384.5 | 1.5 | 1150 | 70.4 | 66.1 | 93.8 | 0.41 |
| 475.5 | 1.5 | 1150 | 69.5 | 65.4 | 94.1 | 0.40 |
| 596.0 | 1.5 | 1150 | 68.3 | 64.4 | 94.3 | 0.39 |
| 695.0 | 1.5 | 1150 | 68.2 | 64.4 | 94.4 | 0.39 |
| 763.5 | 1.5 | 1150 | 67.8 | 64.1 | 94.5 | 0.38 |
| 788.0 | 2.0 | 1150 | 71.9 | 68.1 | 94.8 | 0.32 |
| 813.0 | 2.0 | 1150 | 72.0 | 68.3 | 94.9 | 0.31 |
| \multicolumn{7}{c}{Catalyst C} | | | | | | |
| 67.5 | 2.0 | 1150 | 73.6 | 68.5 | 93.0 | 0.40 |
| 93.0 | 2.0 | 1150 | 73.2 | 68.4 | 93.5 | 0.39 |
| 140.0 | 2.0 | 1100 | 58.3 | 56.0 | 96.1 | 0.30 |
| 213.0 | 1.5 | 1150 | 69.9 | 65.2 | 93.3 | 0.46 |
| 259.0 | 1.5 | 1150 | 70.2 | 65.3 | 93.1 | 0.47 |
| 375.0 | 1.5 | 1150 | 69.6 | 65.0 | 93.3 | 0.49 |
| 468.5 | 1.5 | 1150 | 69.8 | 65.3 | 93.5 | 0.50 |
| 589.5 | 1.5 | 1150 | 70.6 | 66.2 | 93.7 | 0.48 |
| 612.5 | 2.0 | 1150 | 73.3 | 69.2 | 94.4 | 0.38 |
| 637.0 | 2.0 | 1150 | 73.6 | 69.5 | 94.5 | 0.38 |
| 734.5 | 2.0 | 1150 | 74.3 | 70.0 | 94.3 | 0.36 |

EXAMPLE 2

Additional catalyst were made having the same composition as those of Example 1 except for the amount of chromium which was present in the red iron oxide, said chromium having been added to yellow iron hydrate prior to conversion to red iron oxide.

Catalyst D contained 500 ppm chromium.
Catalyst E contained 1000 ppm chromium.
Catalyst F contained no chromium.

Figure 2:
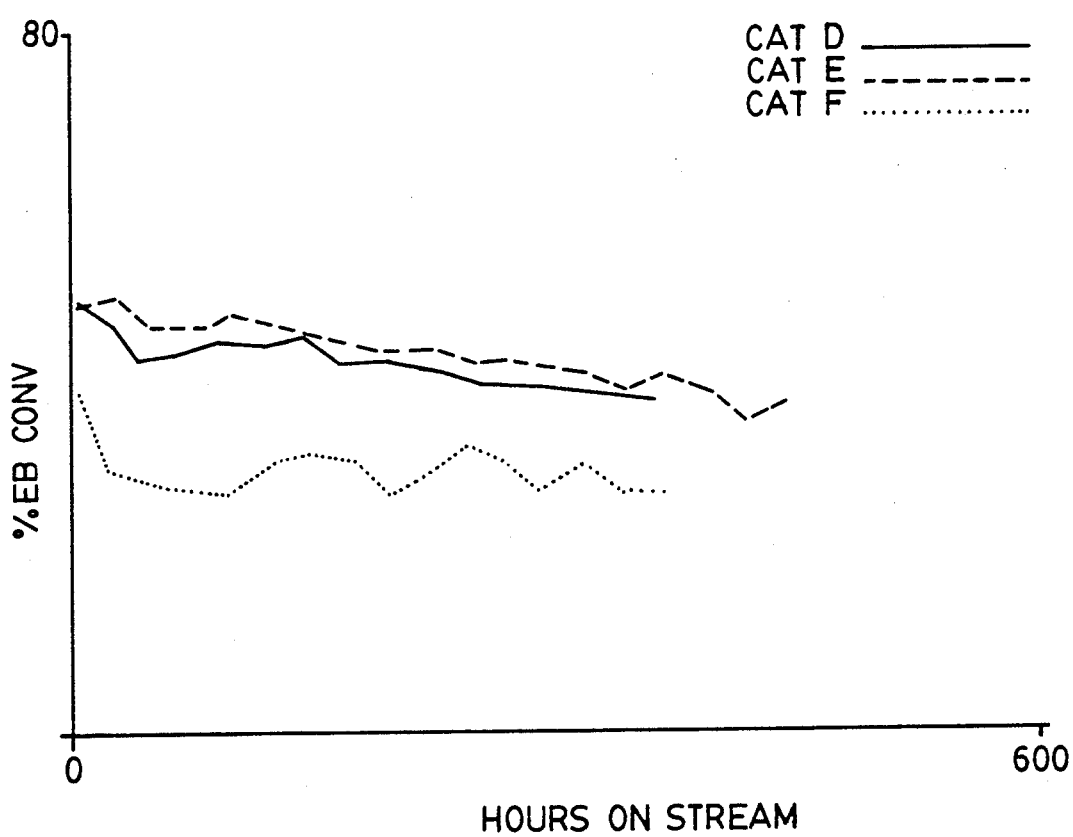

Test data from these reactions are shown in Table II. FIG. 2 is a plot of Percent Ethylbenzene Conversion versus Time on Stream for Catalysts D, E and F. Catalysts D and E again show improved stability when compared to Catalyst F which contained no chromium modification.

TABLE II

Ethylbenzene Dehydrogenation

| Hours | S/O | Temp °F. | Conversion % | Yield % | Selectivity % | B/T |
|---|---|---|---|---|---|---|
| \multicolumn{7}{c}{Catalyst D} | | | | | | |
| 72.5 | 2.0 | 1150 | 75.7 | 40.0 | 92.4 | 0.45 |
| 118.5 | 2.0 | 1100 | 60.9 | 58.3 | 95.6 | 0.33 |
| 147.5 | 1.5 | 1150 | 72.8 | 66.5 | 91.4 | 0.58 |
| 190.0 | 1.5 | 1150 | 71.0 | 65.4 | 92.0 | 0.59 |
| 262.0 | 1.5 | 1150 | 71.4 | 65.7 | 92.0 | 0.60 |
| 311.0 | 1.5 | 1150 | 70.9 | 65.5 | 92.3 | 0.60 |
| 386.5 | 1.5 | 1150 | 70.4 | 65.2 | 92.6 | 0.60 |
| 454.0 | 1.5 | 1150 | 70.1 | 65.1 | 92.9 | 0.58 |
| 501.5 | 1.5 | 1150 | 69.8 | 64.8 | 92.9 | 0.58 |
| 549.0 | 2.0 | 1150 | 73.7 | 69.2 | 93.9 | 0.41 |
| 574.5 | 2.0 | 1150 | 74.3 | 69.6 | 93.7 | 0.40 |
| 597.5 | 2.0 | 1100 | 57.3 | 55.2 | 96.3 | 0.34 |
| 623.0 | 2.0 | 1050 | 36.6 | 35.7 | 97.7 | 0.49 |
| \multicolumn{7}{c}{Catalyst E} | | | | | | |
| 71.5 | 2.0 | 1150 | 75.2 | 69.7 | 92.7 | 0.44 |
| 118.5 | 2.0 | 1150 | 74.7 | 69.4 | 92.9 | 0.42 |
| 144.0 | 2.0 | 1100 | 60.1 | 57.5 | 95.7 | 0.33 |
| 241.5 | 1.5 | 1150 | 72.6 | 66.6 | 91.7 | 0.57 |
| 263.0 | 1.5 | 1150 | 72.9 | 67.0 | 91.9 | 0.56 |
| 312.5 | 1.5 | 1150 | 71.9 | 66.4 | 92.4 | 0.56 |
| 382.0 | 1.5 | 1150 | 71.8 | 66.4 | 92.4 | 0.56 |
| 455.0 | 1.5 | 1150 | 71.4 | 66.2 | 92.7 | 0.58 |
| 502.5 | 1.5 | 1150 | 71.0 | 65.7 | 92.6 | 0.59 |
| 554.5 | 1.5 | 1150 | 70.5 | 65.5 | 93.0 | 0.60 |
| 575.0 | 1.5 | 1150 | 69.8 | 64.9 | 93.0 | 0.61 |
| 669.5 | 1.5 | 1150 | 69.6 | 65.0 | 93.4 | 0.57 |
| \multicolumn{7}{c}{Catalyst F} | | | | | | |
| 71.0 | 2.0 | 1150 | 74.6 | 69.3 | 92.9 | 0.24 |
| 118.5 | 2.0 | 1050 | 44.6 | 43.3 | 97.2 | 0.22 |
| 144.0 | 1.5 | 1150 | 67.9 | 63.1 | 92.9 | 0.29 |
| 240.0 | 1.5 | 1150 | 68.0 | 63.7 | 93.8 | 0.29 |
| 311.5 | 1.5 | 1150 | 67.1 | 63.0 | 93.9 | 0.30 |
| 362.5 | 1.5 | 1150 | 68.6 | 64.6 | 94.2 | 0.30 |
| 454.5 | 1.5 | 1150 | 67.2 | 63.5 | 94.5 | 0.32 |
| 503.0 | 2.0 | 1150 | 70.3 | 66.4 | 94.4 | 0.26 |
| 552.5 | 2.0 | 1150 | 71.3 | 67.3 | 94.4 | 0.25 |

TABLE II-continued

| | | | Ethylbenzene Dehydrogenation | | | |
|---|---|---|---|---|---|---|
| Hours | S/O | Temp °F. | Conversion % | Yield % | Selectivity % | B/T |
| 575.5 | 2.0 | 1100 | 55.4 | 53.4 | 96.4 | 0.24 |
| 598.5 | 2.0 | 1050 | 36.0 | 35.2 | 97.8 | 0.33 |

EXAMPLE 3

Figure 3:
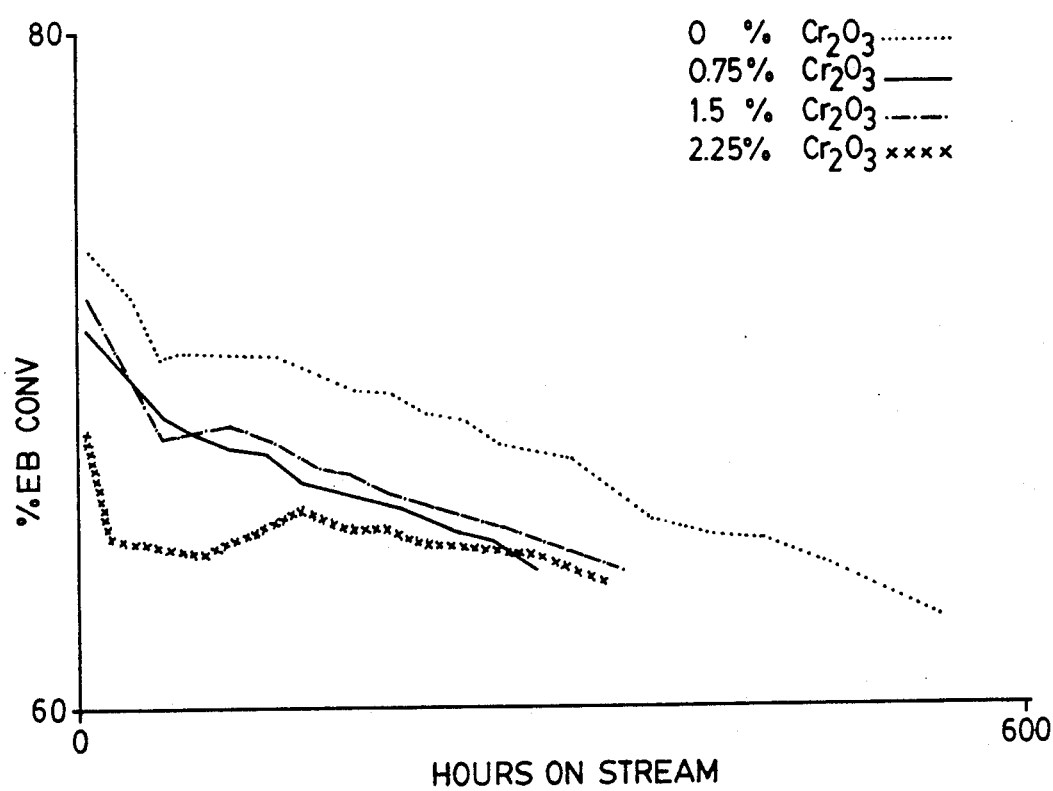
FIG. 3 is a plot of weight percent ethylbenzene conversion versus hours on stream using catalysts containing chromium oxide which was added during formation of the catalyst and catalysts which contained no chromium oxide.

Catalysts were prepared using the same procedure and components as described in Example 1 except chromium oxide was added during the preparation of the catalysts and not preadded to yellow iron hydrate prior to its conversion to red iron oxide. The amounts of chromium oxide added were 0.75 percent, 1.5 percent, and 2.25 percent based on the weight of the catalyst. When used as catalysts for the dehydrogenation of ethylbenzene to styrene, the conversion, selectivity, and stability were inferior to the catalysts which contained no added chromium oxide. FIG. 3 is a plot of Weight Percent Ethylbenzene Conversion vs. Time on Stream for each of these catalysts.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. A process for preparing a dehydrogenation catalyst containing a major amount of red iron oxide and a mintor amount of chromium oxide and additionally an alkali metal oxide, an alkaline earth metal oxide, an oxide of a lanthanide having atomic numbers of 57 to 62, and oxide or molybdenum or tungsten, the improvement which comprises, prior to forming the catalyst, mixing chromium oxide or a chromium salt with yellow iron hydrate and heating the mixture to convert the yellow iron hydrate to red iron oxide.

2. The process of claim 1 wherein chromium oxide or salt is added to the yellow iron hydrate in an amount sufficient to obtain about 100 to about 5000 ppm chromium in the red iron oxide wherein said ppm are based on the weight of chromium and red iron oxide.

3. The process of claim 2 wherein the amount of chromium is about 100 to about 1200 ppm.

4. The process of claim 1 wherein the mixture of chromium oxide or salt and yellow iron hydrate is obtained by coprecipitation of the chromium salt and yellow iron hydrate.

5. The process of claim 1 wherein the mixture of chromium oxide or salt and yellow iron hydrate is obtained by blending the chromium oxide or salt with the yellow iron hydrate after it is formed.

6. The process of claim 1 wherein the mixture of yellow iron hydrate and chromium oxide or salt is heated to about 500° C. to about 1000° C. for a time sufficient to convert the yellow iron hydrate to red iron oxide.

7. The process of claim 1 wherein the catalyst contains about 60 to about 90 weight percent red iron oxide modified with 100 to 5000 ppm chromium, about 5 to about 15 weight percent alkali metal oxide, about 2 to about 10 weight percent alkaline earth metal oxide, about 2 to about 10 weight percent oxide of a lanthanide and about 1 to about 5 weight percent oxide of molybdenum or tungsten.

8. The process of claim 7 wherein the alkali metal oxide is sodium or potassium oxide, the alkaline earth metal oxide is magnesium, calcium, or strontium oxide, and the oxide of the lanthanide is cerium, praseodymium, neodynium, or samarium oxide.

9. The process of claim 8 wherein the catalyst contains about 80 to about 86 weight percent red iron oxide modified with 100 to 1200 ppm chromium, about 7 to about 12 weight percent potassium oxide, about 3 to about 7 weight percent cerium oxide, about 1 to about 4 weight percent molybdenum oxide, and about 1.5 to about 3.5, weight percent magnesium oxide.

10. A dehydrogenation catalyst comprised of red iron oxide, an alkali metal oxide, an alkaline earth metal oxide, an oxide of a lanthanide having atomic numbers of 57 to 62, and molybdenum or tungsten oxide wherein said red iron oxide is modified with chromium oxide wherein said modification is obtained prior to forming said catalyst by mixing chromium oxide or a chromium salt with yellow iron hydrate and heating the mixture to convert the yellow iron hydrate to red iron oxide.

11. The catalyst of claim 10 wherein the chromium oxide is present in the red iron oxide in the amount of about 100 to about 5000 ppm chromium wherein said ppm are based on the weight of chromium and the red iron oxide.

12. The catalyst of claim 11 wherein the red iron oxide, is modified with about 100 to about 1200 ppm chromium.

13. The catalyst of claim 11 wherein the red iron oxide is present in the amount of about 60 to about 90 weight percent to about 5 to about 15 weight percent alkali metal oxide, about 2 to about 10 weight percent alkaline earth metal oxide, about 2 to about 10 weight percent oxide of a lanthanide and about 1 to about 5 weight percent oxide of molybdenum or tungsten.

14. The catalyst of claim 13 wherein the alkali metal oxide is sodium or potassium oxide, the alkaline earth metal oxide is magnesium, calcium, or strontium oxide, and the oxide of a lanthanide is cerium, praseodymium, neodymium, or samarium oxide.

15. The catalyst of claim 12 which contains about 80 to about 86 weight percent red iron oxide, about 7 to about 12 weight percent potassium oxide, about 3 to about 7 weight percent cerium oxide, 1 about 1 to about 4 weight percent molybdenum oxide, and about 1.5 to about 3.5 weight percent magnesium oxide.

* * * * *